US00PP30705P2

(12) United States Plant Patent
Cain

(10) Patent No.: US PP30,705 P2
(45) Date of Patent: Jul. 16, 2019

(54) GRAPEVINE PLANT NAMED 'IFG THIRTY-SIX'

(50) Latin Name: ***Vitis interspecific* hybrid**
Varietal Denomination: IFG Thirty-six

(71) Applicant: David Cain, Bakersfield, CA (US)

(72) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 24 days.

(21) Appl. No.: 15/932,108

(22) Filed: Feb. 5, 2018

(51) Int. Cl.
*A01H 5/08* (2018.01)
*A01H 6/88* (2018.01)

(52) U.S. Cl.
USPC ..... Plt./205
CPC ..... *A01H 6/88* (2018.05); *A01H 5/08* (2013.01)

(58) Field of Classification Search
USPC ..... Plt./205
CPC ..... A01H 5/0812
See application file for complete search history.

(56) References Cited

PUBLICATIONS

U.S. Appl. No. 15/732,705 P1, filed Dec. 13, 2017, Cain.

*Primary Examiner* — Kent L Bell

(57) ABSTRACT

This invention is a new and distinct grapevine variety denominated 'IFG Thirty-six'. The new grapevine is characterized by producing naturally large seedless black berries having a broad ellipsoidal shape with a strong spicy concord-like labrusca flavor. Fruits are medium in acidity, with a firm texture and have excellent eating quality. Berries color readily even in hot climatic conditions and produce completely colored black berries. Vines are productive and can be pruned to short spurs.

1 Drawing Sheet

Latin name of the genus and species claimed: *Vitis interspecific* hybrid.

Variety denomination: 'IFG THIRTY-SIX.'

BACKGROUND OF THE INVENTION

The new and distinct grapevine plant described and claimed herein originated from a hand pollinated cross of '01161-040-184' (unnamed *Vitis vinifera* selection from the IFG breeding program), and 'IFG Thirty-four' (U.S. Plant Pat. No. 30,325) hybridized in May 2008. The abortive seed traces were subsequently embryo cultured and the resulting 245 plants were planted in the field in April 2009. The present variety of grapevine was selected as a single plant in September 2011 and was first asexually propagated by hardwood cuttings in December 2011 near Delano, Kern County, Calif. These resulting cuttings produced second generation plants that were planted during April 2012 near Delano, Kern County, Calif. were observed for four years and found to reproduce true-to-type.

BRIEF SUMMARY OF THE INVENTION

The new grapevine plant 'IFG Thirty-six' is characterized by producing naturally large seedless black berries having a broad ellipsoidal shape with a strong spicy concord-like labrusca flavor. Fruits are medium in acidity, with a firm texture and have excellent eating quality. Berries color readily even in hot climatic conditions and produce completely colored black berries. Vines are productive and can be pruned to short spurs. Clusters are medium size, and often do not set enough berries which can be ameliorated by tipping before bloom. Berry size can be increased by applying gibberellic acid.

'IFG Thirty-six' can be distinguished from its maternal parent, the 01161-040-184, by having larger berry size, less firm flesh, a more completely black color and by having a strong spicy concord-like labrusca flavor as opposed to the neutral vinifera flavor of 01161-040-184.

The new grapevine differs from its pollen parent the 'IFG Thirty-four' by having more fully black rather than reddish black to black berry color; by having a broad ellipsoidal rather than round shape and by having much larger natural berry size and by having a larger cluster size and firmer berries.

'IFG Thirty-six' is most similar to its sibling the 'IFG Twenty-two' (U.S. Plant Pat. No. 26,541), but differs from 'IFG Twenty-two' by having a smaller cluster size, larger berry size, a broad ellipsoidal berry shape as opposed to a round to slightly elliptic shape of 'IFG Twenty-two', and a more completely black color. It also has a distinctly different flavor being more spicy and less artificial grape candy-like.

'IFG Thirty-six' is somewhat similar to its other sibling, 'IFG Thirty-seven' (PPAF 15/932,107). IFG Thirty-six' differs from 'IFG Thirty-seven' by having a black rather than a red berry color and by having a stronger, more spicy labrusca flavor.

'IFG Thirty-six' is also somewhat similar to the Tomcord (non-patented) variety. It differs from the 'Tomcord' by having larger berry size, by having smaller residual seed traces, and by having a looser more open cluster density.

Grape breeders have used several native American grape species to improve hardiness, disease and insect resistance as well as incorporate aromatic flavors into the vinifera species. Previously introduced interspecific varieties have had very limited commercial success due to small fruit size, large seed traces, and slip skin texture. The new grapevine variety is being introduced because of its excellent concord-like flavor combined with seedlessness, and good adhesion of skin to flesh combined with naturally large berry size.

BRIEF DESCRIPTION OF THE DRAWING

The accompanying photographic drawing in FIG. 1 illustrates in full color 'IFG Thirty-six', taken from a 4-year-old vine. The photograph was taken outdoors with indirect lighting. The colors are as nearly true as is reasonably possible in a color representation of this type. The left side of the drawing has mature leaves. A mature fruit cluster is represented in the center of the drawing along with a typical berry in cross section. A young shoot with tendrils can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2015 by The Royal Horticultural Society, London, England.

Throughout this specification, subjective description values conform to those set forth by the UPOV International Union for the Protection of New Varieties of Plants publication 'Grapevine Vitis L. Guidelines'.

The descriptive matter which follows pertains to 'IFG Thirty-six' plants grown in the vicinity of Delano, Kern County, Calif. during 2017, and is believed to apply to plants of the variety grown under similar conditions of soil and climate elsewhere:

VINE

General:
- *Vigor.*—Vigorous.
- *Density of foliage.*—Dense.
- *Productivity.*—Medium productive, producing about 20.2 to 30.3 kg of fruit per vine.
- *Root stock.*—Own root.
- *Training method.*—Typically spur pruned leaving 2 bud spurs.

Trunk:
- *Trunk diameter of* 4-*year-old vines at* 30 *cm above the soil line.*—About 5.3 cm.
- *Shape.*—Medium stout.
- *Straps.*—Short, split.
- *Surface texture.*—Shaggy texture.
- *Inner bark color.*—The following colors were observed: Greyed-orange: 174A and 174B and 174C.
- *Outer bark color.*—Grey: 201A.

SHOOTS

Young shoot:
- *Form of tip.*—Fully opened.
- *Distribution of anthocyanin coloration of tip.*—Absent.
- *Intensity of anthocyanin coloration of tip.*—Absent.
- *Density of prostrate hairs of tip.*—Sparse.
- *Density of erect hairs on tip.*—Absent.
- *Color.*—Yellow-green: 146B.

Woody shoot (Mature canes):
- *Internode length.*—Long: About 13.5 cm.
- *Width at node.*—About 1.4 cm.
- *Cross section.*—Circular.
- *Surface.*—Striate.
- *Main color.*—The following colors were observed: Greyed-orange: 165A and 165B and 165C and 164A and 166A.
- *Density of erect hairs on nodes.*—None or very sparse.
- *Density of erect hairs on internodes.*—None.
- *Axillary shoot length at full bloom.*—Strong: Approximately 24.4 cm.

Flowering shoot:
- *Vigor during flowering.*—Strong.
- *Attitude during flowering on shoots not tied.*—Semi-erect.
- *Color.*—Dorsal side of internodes — Yellow-green: 146C, with Red-purple stripes: 59B.
- *Color.*—Ventral side of internodes — Yellow-green: 146C.
- *Color.*—Dorsal side of nodes — Yellow-green: 146C.
- *Color.*—Ventral side of nodes — Yellow-green: 146C.
- *Density of prostrate hairs on nodes.*—Very sparse.
- *Density of erect hairs on nodes.*—None.
- *Density of prostrate hairs on internode.*—None to very sparse.
- *Density of erect hairs on internode.*—None.
- *Anthocyanin coloration of buds.*—Absent.

Tendrils (at full bloom):
- *Distribution on the shoot* (*at full flowering*).—Discontinuous.
- *Length of Tendril.*—Long: about 26.6 cm.
- *Thickness of tendril* 2 *cm from base.*—About 2.6 mm.
- *Color.*—Yellow-green: 144B.
- *Form.*—Trifurcated.
- *Number of consecutive tendrils.*—2.

LEAVES

Young leaves:
- *Color of upper surface of first four distal unfolded leaves.*—Yellow-green: 146A.
- *Color of lower surface of young leaves.*—Yellow-green: 145A and 151B.
- *Average intensity of anthocyanin coloration of six distal leaves prior to flowering.*—Absent.
- *Density of prostrate hairs between veins* (*lower surface*).—Absent.
- *Density of prostrate hairs on veins* (*lower surface*).—Sparse.
- *Density of erect hairs between veins* (*lower surface*).—Absent.
- *Density of erect hairs on veins* (*lower surface*).—Very sparse.

Mature leaves:
- *Average length.*—About 15.8 cm.
- *Average width.*—About 19.8 cm.
- *Mature leaf size.*—Large.
- *Shape of blade.*—Wedge-shaped.
- *Number of lobes.*—5.
- *Blade venation.*—Palmate.
- *Anthocyanin coloration of main veins on upper side of blade.*—Absent.
- *Mature leaf profile.*—Flat.
- *Blistering surface of blade upper surface.*—Weak.

*Leaf blade tip.*—In the plane of the leaf.
*Leaf apex.*—Acute.
*Leaf margin.*—Serrate.
*Undulation of margin.*—Slight.
*Undulation of blade between main and lateral veins.*—Absent.
*Shape of teeth.*—Mixture of both sides straight and both sides convex.
*Length of teeth.*—Long.
*Ratio length/width of teeth.*—Medium.
*Shape of upper lateral sinuses.*—Lobes slightly overlapping.
*Depth of upper lateral sinuses.*—Medium.
*General shape petiole sinus.*—Half open overlapping.
*Shape of base of upper leaf sinuses.*—V-shaped.
*Tooth at petiole sinus.*—Absent.
*Density of prostrate hairs between veins on lower surface of blade.*—Absent.
*Density of erect hairs between veins on lower surface of blade.*—Absent.
*Density of prostrate hairs on main veins on lower surface of blade.*—Sparse.
*Density of erect hairs on main veins on lower surface of blade.*—Sparse.
*Density of prostrate hairs on main veins on upper surface of blade.*—Very sparse.
*Density of erect hairs on main veins on upper surface of blade.*—None.
*Autumn coloration of leaves.*—Greyed-yellow: 161A.

Upper surface:
*Color.*—Green: NN137A.
*Anthocyanin coloration of main veins (lower surface).*—Absent.
*Color of main veins.*—Yellow-green: 144C.
*Surface appearance.*—Dull.
*Blistering surface of blade.*—Medium.

Lower surface:
*Color.*—Yellow-green: 147B.
*Anthocyanin coloration of main veins (lower surface).*—Absent.
*Color of main veins.*—Yellow-green: 145C.
*Glossiness.*—Weak.
*Surface texture.*—Rugose.
*Surface appearance.*—Dull.

Petiole:
*Length.*—About 13.0 cm.
*Diameter of petiole 2 cm from blade.*—About 3.1 mm.
*Petiole color.*—Yellow-green: 145C.
*Length of petiole compared to middle vein.*—Slightly shorter.
*Density of prostrate hairs on petiole.*—None.
*Density of erect hairs on petiole.*—None.

Buds:
*Bud fruitfulness.*—Basal: mostly fruitful.
*Position of first fruitful shoot on previous season cane.*—$1^{st}$ to $2^{nd}$ node.
*Dormant bud length.*—About 5.5 mm.
*Dormant bud width in the proximal/distal plane.*—About 5.1 mm.
*Dormant bud color.*—Greyed-orange: 166A.
*Time of bud burst.*—Mid-season: About Mar. 16, 2017.

FLOWERS

General:
*Flower sex.*—Hermaphrodite.
*Length of single flower, unopened.*—About 3.7 mm.
*Width of single flower.*—Unopened: About 2.2 mm. Opened: About 7.0 mm.
*Stamen length.*—About 3.5 mm.
*Stamen count.*—5.
*Pollen color.*—Yellow: 10B.
*Pistil length.*—About 3.2 mm.
*Pistil color.*—Yellow-green: 146A.
*Length of first inflorescence.*—Medium: About 16.1 cm long by 11.6 cm wide.
*Position of first flowering and fruiting node.*—$3^{rd}$ to $4^{th}$ (current season growth).
*Number of inflorescence per flowering shoot.*—1.1 to 2: About 2.
*Time of bloom.*—Mid-season as compared with similar varieties in the growing area of Delano, Calif.
*Date of full bloom.*—About May 10, 2017.

FRUIT

General:
*Ripening period.*—Early: Approximately Jul. 20, 2017.
*Use.*—Fresh market.
*Keeping quality.*—Good, remains commercially acceptable when stored up to 8 weeks at 0° C. and high RH.
*Resistance to.*—Insects: Average typical of *Vitis vinifera* species. Diseases: Average typical of *Vitis vinifera* species.
*Refractometer test.*—Soluble solids: About 19.0 Brix.
*Brix/acid.*—About 32.8.
*% Titratable acidity.*—About 0.58.
*Juice pH.*—About 3.67.

Cluster:
*Mature cluster length (peduncle excluded).*—About 26.2 cm.
*Mature cluster width.*—About 15.8 cm.
*Mature cluster weight.*—About 673 g.
*Bunch density.*—Loose: single berries, some pedicels visible.
*Number of berries.*—About 65.
*Form.*—Conical.

Peduncle:
*Lignification of peduncle.*—Weak.
*Diameter of peduncle.*—About 5.0 mm.
*Length of peduncle.*—Medium: Approximately 3.2 cm.
*Color of peduncle.*—Yellow-green: 145A.

Berry:
*Uniformity of size.*—Uniform.
*Single berry weight.*—About 12.3 g natural.
*Shape.*—Broad ellipsoid.
*Seeds.*—Absent.
*Cross section.*—Circular.
*Berry dimensions.*—Longitudinal axis: about 3.0 cm; horizontal axis: about 2.5 cm.
*Pedicel length.*—About 11.4 mm.
*Pedicel width.*—About 2.7 mm.
*Pedicel color.*—Yellow-green: 144C.
*Berry firmness.*—Firm.
*Particular flavor.*—Spicy labrusca.
*Bloom (cuticular wax).*—Strong.
*Berry separation from pedicel.*—Medium.
*Skin color (without bloom).*—The following colors were observed: Greyed-purple: N186A and N186B.
*Flesh color.*—Green-white: 157D.

Skin:

*Thickness.*—Medium-thick.

*Skin toughness.*—Somewhat notable when chewing.

*Reticulation.*—Absent.

*Tenacity.*—Tenacious to flesh.

What is claimed:

1. A new and distinct variety of grapevine plant as herein illustrated and described.

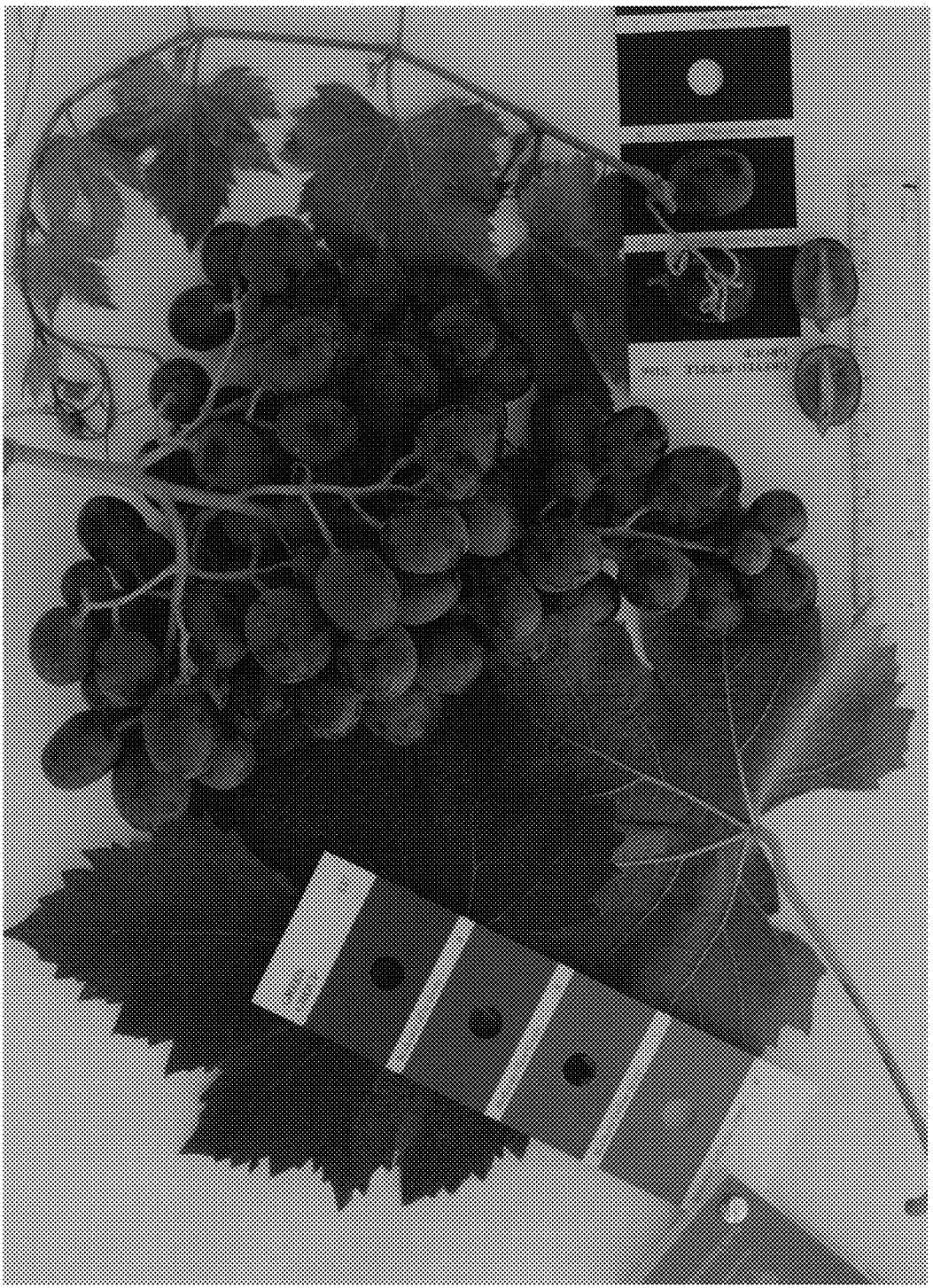

* * * * *